United States Patent [19]

Sikdar et al.

[11] Patent Number: 4,469,561
[45] Date of Patent: Sep. 4, 1984

[54] AZEOTROPIC RECOVERY OF BPA AND PHENOL FROM AQUEOUS EFFLUENT STREAMS

[75] Inventors: Subhas K. Sikdar, Clifton Park; Viney P. Aneja, Schenectady, both of N.Y.

[73] Assignee: General Electric Company, Schenectady, N.Y.

[21] Appl. No.: 458,382

[22] Filed: Jan. 17, 1983

Related U.S. Application Data

[63] Continuation of Ser. No. 279,373, Jul. 1, 1981, abandoned.

[51] Int. Cl.³ .......................... E01D 3/34; E01D 3/36
[52] U.S. Cl. .................................... 203/39; 568/748; 568/752

[58] Field of Search ............... 568/727, 724, 748, 753, 568/750, 751, 752; 203/39, 43–46

[56] References Cited

U.S. PATENT DOCUMENTS 2,959,622  11/1960  Grimme et al. ..................... 568/724
3,277,183  10/1966  Heller et al. ........................ 568/724

Primary Examiner—Frank Sever
Attorney, Agent, or Firm—William A. Teoli; James C. Davis, Jr.; James Magee, Jr.

[57] ABSTRACT

A method for simultaneously extracting and recovering 2,2-bis(4-hydroxy phenyl) propane and phenol from aqueous effluent streams by liquid-liquid extraction using toluene.

6 Claims, 1 Drawing Figure

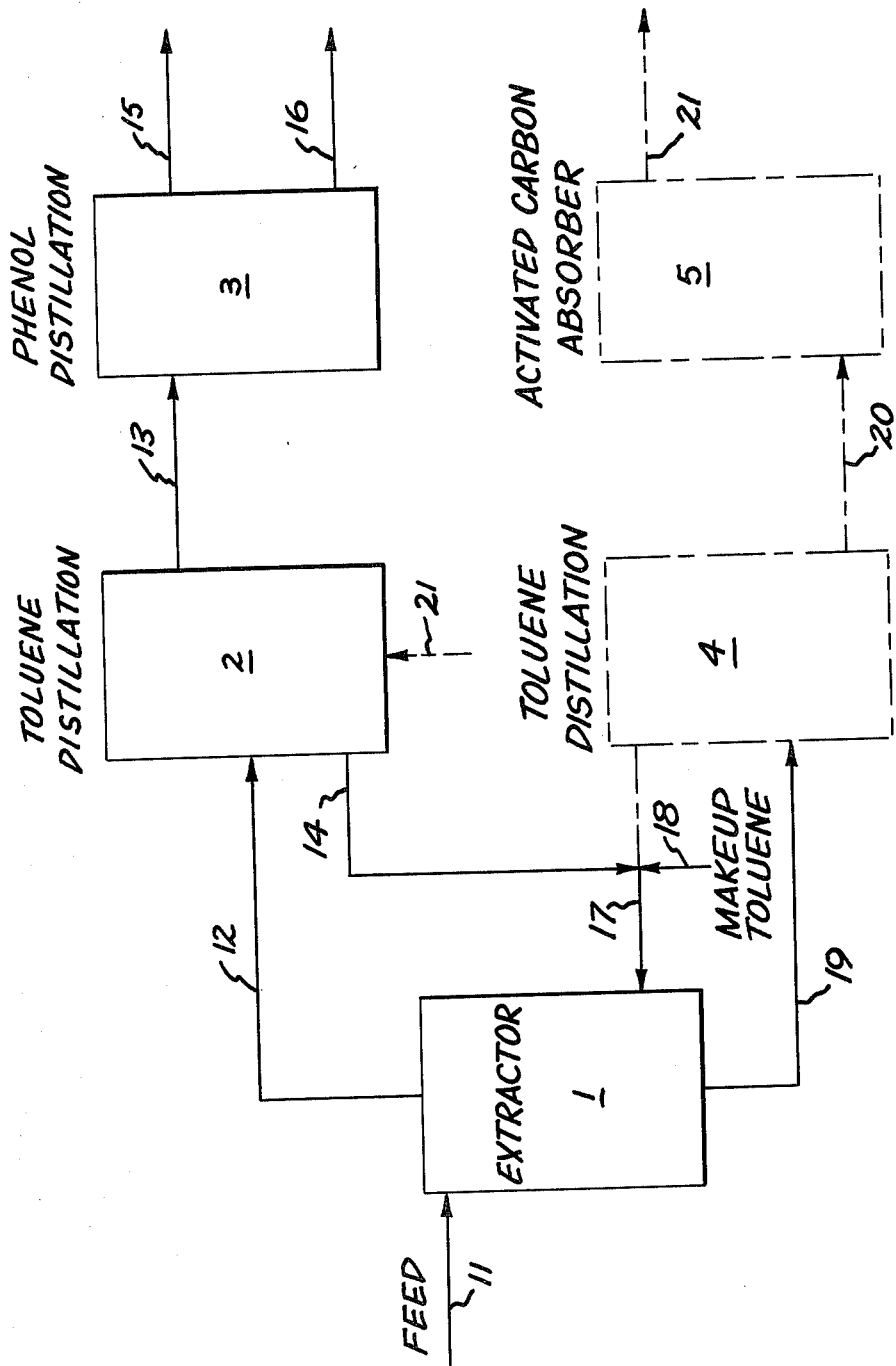

AZEOTROPIC RECOVERY OF BPA AND PHENOL FROM AQUEOUS EFFLUENT STREAMS

This application is a continuation of application Ser. No. 279,373, filed July 1, 1981, abandoned.

This invention is concerned with the recovery of 2,2-bis (4-hydroxyphenyl) propane (hereinafter identified as "bisphenol A" or BPA) and phenol from aqueous effluent streams. More particularly the invention is directed to the simultaneous extraction and azeotropic recovery of BPA and phenol from aqueous effluent streams by liquid-liquid extraction using toluene as the extraction solvent. The BPA and phenol are recovered in a substantially pure state for potential recycling by a subsequent distillation step leaving toluene which can be reused in the extraction process and water which can be disposed of without adverse environmental consequences.

Cross-reference is made to application U.S. Pat. Nos. 4374283 and DN4400553 assigned to the same assignee as the present invention.

BPA is commercially prepared by reacting phenol and acetone in the presence of either an acidic material such as sulfuric acid, hydrochloric acid, etc., or a cationic exchange resin. As a result of carrying out this reaction the BPA produced is accompanied by many undesirable impurities such as other impurities including phenol itself used in making the BPA.

Since bisphenol A is used in making polycarbonate resins by reaction of the latter with either phosgene or diphenylcarbonate, or for making epoxy resins, both resins being used extensively in commercial applications involving molding, casting, and sheet forming purposes, it is highly important that the monomeric bisphenol A used to make such resins be as pure as possible in order to avoid adverse effects on the properties of the polymers thus obtained.

The preparation of the bisphenol A by the reaction of phenol and acetone often leads to an adduct in which there is 1 mol of phenol per mol of the bisphenol-A together with any excess phenol which may have been used for reaction purposes. One method for working with this adduct to arrive at a purified bisphenol-A product is described in Luten U.S. Pat. No. 2,791,616. According to this patent the adduct obtained as a result of carrying out the initial reaction in the presence of the acidic condensation catalyst, is washed with an excess amount of water within a well defined temperature range which serves to liberate the phenol from the adduct with the result that essentially all the phenol is dissolved in the water while substantially all the bisphenol-A remains behind in the solid state. However, this process suffers from several disadvantages. Excessive amounts of water are usually required. Also, the water obtained containing the phenol, whether liberated from the adduct or the excess amount used in carrying out the initial condensation reaction, is in the form of a solution or mixture containing both BPA and phenol. This solution or mixture requires considerable processing and expenditure of energy in order to recover the BPA and phenol so that they can be used or the phenol recycled again for reaction with acetone and so that the aqueous portion can be disposed of without having to deal with the presence of phenol, which is toxic at very low levels, or with other contaminants produced by the reactions.

Phenol is among the more obnoxious of the contaminants which are present in the aqueous effluent from the aqueous purification process, its taste and odor are detectable in water concentrations of less than 4 ppm, it gives an objectionable odor to fish at 1 ppm, and it is toxic to some species of fish at concentrations as low as 0.1 ppm. In addition, when water containing phenol is chlorinated, chlorophenols are produced which give the water an objectionable taste and odor at concentrations as low as 0.001 ppm. In general, the phenol content of industrial effluents is required to be less than 1 ppm. In the absence of any U.S. government regulatory standards on BPA its content in industrial effluents is assumed to also be less than 1 ppm.

In a BPA manufacturing process which employs aqueous purification steps such as, for example, crystallization, washing, extraction, etc. substantial quantities of BPA and phenol, for example, in the order of 6%, by weight, for each are retained as major organic compounds in the aqueous stream after the aqueous purification step. These must be recovered and or disposed of in an acceptable manner. At these large concentrations there exist strong economic and environmental incentives for recovering both BPA and phenol from the aqueous effluent streams simultaneously.

Among the processes which can be used to recover BPA and toluene from aqueous effluent streams, solvent extraction is generally preferable over steam stripping for the removal of phenols, since the phenol-water system forms a minimum boiling azeotrope at 9.2 weight % phenol. Activated carbon and resin bed adsorption have been used but the processing costs become substantial at the higher concentrations encountered here. Reverse osmosis with cellulose acetate or thin-film composite membranes is not possible. Other permeators have a limiting phenol concentration of about 5,000 ppm above which they are impractical because of their inherent design features.

The solvent most suited for the extraction of phenol from water is methyl isobutyl ketone, hereinafter also referred to as "MIBK", because of its high equilibrium distribution coefficient. A method for the simultaneous extraction and recovery of BPA and phenol from aqueous streams is described in a application U.S. Pat. No. 4400553 of V. P. Aneja filed concurrently with the present application and assigned to the same assigne as the present invention. Measurements of the equilibrium distribution coefficients of BPA in phenol water and MIBK, and phenol in BPA water and MIBK, show that direct simultaneous extraction of BPA and phenol with MIBK is extremely effective.

However, there is some concern that the phenol recycle stream may contain trace quantities, for example, $\leq 10$ ppm of MIBK which may adversely affect the performance of the BPA reaction and purification used in the manufacture of BPA, hence, it is necessary to find an alternative extracting solvent to MIBK which is either inert or does not adversely affect the performance of the BPA reaction and purification steps. It was found that toluene could replace MIBK as the extracting solvent since toluene has an extraction factor sufficiently high for both BPA and phenol for the temperature range of interest, for example up to 60° C. Also toluene does not appear to adversely affect the performance of the BPA reaction and purification used in the manufacture of BPA.

For MIBK the equilibrium distribution coefficient at 30° C.±1° C. was found to $\geq 2000$ for BPA between phenol plus water and MIBK, and ≧60 for phenol between BPA plus water and MIBK. At 60° C.±1° C. the equilibrium distribution coefficient was ≧1000 for BPA between phenol plus water and MIBK and ≧40 for phenol between BPA plus water and MIBK.

For toluene the equilibrium distribution coefficient at 30° C.±2° C. was found to be about 30 for BPA between phenol plus water and toluene, and about 3 for phenol between BPA plus water and toluene. At 60° C.±1° C. the equilibrium distribution coefficient was about 25 for BPA between phenol plus water and toluene and about 3 for phenol between BPA plus water and toluene.

There is no doubt that these differences in equilibrium distribution coefficients would have a large effect on process economics, since large distribution coefficients allow efficient extraction. However, there are factors which make the use of toluene, as an extracting solvent, more desirable:

(1) toluene does not appear to adversely affect the performance of BPA reaction and purification used in the manufacturing process.

(2) the water entrained in the organic stream is removed as a toluene-water azeotrope and recycled to the extractor without separation. The minimum boiling azeotrope of toluenewater, which has a boiling point of 84° C. at 80% toluene, assures complete removal of water from the BPA-phenol stream.

(3) the equilibrium distribution coefficient with toluene for BPA and phenol scarcely vary with temperature.

(4) toluene is relatively insoluble in water. This lower solubility permits less toluene to be carried through the extraction in the aqueous phase and, in many cases, may obviate the need for solvent removal from the aqueous phase if the toluene load is small. However, if necessary, the effluent stream can be cleaned by simply using activated charcoal or an organic resin. Because toluene is insoluable in water and essentially all of the toluene is or can be removed, this process could therefore lead to a process for obtaining a highly purified water product from the BPA purification effluent.

The equilibrium distribution coefficient of the solvent is very important since it affects the required ratio of solvent mass flow rate to aqueous mass flow rate in continuous extraction. The distribution coefficient of toluene allows efficient BPA and phenol extraction at relatively low solvent ratios and allows efficient extraction with recycled toluene which has been less thoroughly regenerated. Moreover the specific gravity of toluene, 0.87 at 20° C., is sufficiently different from that of water, 0.989 at 20° C., so that countercurrent flow in a continuous extraction column or settling in a mixer-settler will proceed readily.

The extraction can be carried out in a conventional extraction column using countercurrent or cocurrent exchange flows. Countercurrent extraction is the preferred method. Using this method the heavy phase (water containing BPA and phenol) enters at the top and the light phase (or toluene) enters at the bottom of the column. The toluene extract containing BPA and phenol must be treated to recover the BPA and Phenol and to regenerate the toluene for reuse in the extraction.

It was found that azeotropic distillation is the best method for separating the BPA and phenol from the loaded solvent. The toluene extract containing BPA and phenol is sent to a distillation column to separate the BPA and phenol from toluene. Any water entrained in the organic stream is removed as a toluene-water azeotrope and recycled to the extractor without separation. The minimum boiling azeotrope of toluene water (b.p. 84° C., 80% toluene) assures complete removal of water from BPA-phenol stream. This minimum boiling azeotrope boiling point is much different from the boiling points of BPA, 220° C., at 4 mm Hg, and phenol, 181° C. at 1 atmosphere. The addition of water, for example a portion of the aqueous phase from extractor 1, to the toluene distillation vessel 2 will help assure the essentially complete removal of both water and toluene. The concentration in the vessel preferably should be kept near the minimum boiling point of the azeotrope which is 84° C. at 80% toluene. Also the high boiling impurities will not accumulate in the recycle toluene stream. This is desirable since these impurities would be expected to change the equilibrium distribution coefficients and the physical properties of the solvent toluene. The column distillate contains toluene which can be recycled back to the extraction column. The BPA and phenol obtained as a bottoms product can be further separated by diftillation.

The water leaving the extraction column, as the raffinate phase, is saturated with toluene and contains only trace quantities of BPA and phenol. This aqueous stream can be passed to a distillation vessel to recover the trace of toluene as a toluene-water azeotrope. Toluene can be recycled back to the extraction column for reuse. The effluent water containing trace quantities of BPA and phenol and toluene can be further purified, if needed, by activated charcoal or an organic resin.

It has been discovered that bisphenol A and phenol can be extracted for reuse simultaneously from the aqueous effluent stream from a BPA manufacturing process using toluene as the extracting solvent. By using toluene in a liquid-liquid extraction the aqueous effluent stream from the purification step in the BPA manufacturing process can be cleaned to a point where the aqueous portion can be disposed of in an environmentally safe manner without additional treatment. All of the chemicals; BPA, phenol, and toluene, and water are recovered in a sufficiently pure state for recycling. The BPA, phenol and toluene in the organic phase are separated and purified by subsequent distillation and the toluene is optionally removed from the aqueous phase by, for example, distillation. There are both strong economic and strong environmental incentives for using this new process since large amounts of BPA and phenol can be conserved for recycling and in addition the resulting aqueous effluent stream from the BPA purification step can be cleaned of both BPA and phenol to a point where it can be disposed of in a conventional manner with little or no subsequent treatment and at minimum cost.

It has been discovered that the recovery of BPA and phenol from an aqueous effluent stream containing dissolved or suspended BPA and phenol can be accomplished by a continuous process for the simultaneous extraction and recovery of BPA and phenol using a liquid-liquid extraction with toluene as the extraction medium. This recovery is achieved by means of a continuous process comprising the following steps:

(a) introducing an aqueous stream containing BPA and phenol to an extraction vessel along with toluene, (b) removing the heavy aqueous phase from the extraction vessel for further processing or disposal, (c) removing from the top of said extraction vessel a toluene solution of BPA and phenol and, (d) recovering the BPA and phenol from said toluene solution of BPA and phenol and recycling the toluene to said extraction vessel.

According to the present process there may be conveniently used aqueous solutions or suspensions containing dissolved or particulate BPA and phenol. Typical aqueous concentrations can range up to 30% BPA, by weight, and up to 15% phenol, by weight, and more particularly up to 10 percent BPA and up to 5 percent phenol, by weight.

Solutions with low concentrations of BPA and phenol such as those obtained from the aqueous purification steps of conventional BPA manufacturing processes are particularly suitable for use in the practice of this invention. The purified or cleaned aqueous phase obtained using the process of the present invention still contains trace quantities of toluene, phenol and BPA which may optionally be removed by means of further processing steps, e.g. by passing the aqueous phase over activated charcoal or by using an organic resin.

The temperature at which the liquid-liquid extraction vessel is operated will be based upon economic considerations and will generally fall within the range of 20° C. to 80° C. and more particularly between 25° C. and 35° C. The temperature after the purification step in the manufacture of BPA is approximately 60° C. However, the solvent extraction process is somewhat more efficient at lower temperatures, e.g. approximately 30° C. The cost of cooling the aqueous effluent of the BPA purification step versus the lowered extraction efficiency at the higher temperature will dictate the extraction temperature used in individual processes.

By the use of the process of the present invention using liquid-liquid extraction with toluene solvent for simultaneously extracting BPA and phenol from an aqueous effluent stream it is possible to recover essentially all of the chemicals for recycling. BPA, phenol and toluene are recovered by distillation. The process of the present invention would lead to considerable economic benefits since large quantities of BPA and phenol could be recovered. Moreover, only one extraction solvent is being used which results in substantial reduction in solvent recovery and distillation costs when compared to a multiple solvent extraction process. The water effluent can then either be recycled in the process or discharged directly since it will substantially conform to environmental effluent standards.

The weight ratio of toluene extractant to aqueous feed stream, will depend upon the concentrations of BPA and phenol in the feed stream of the degree of recovery desired. Typical ratios can range from 0.1 parts to 2.0 parts by weight toluene per part of aqueous feed with a preferred ratio of about 0.5 parts toluene by weight per part of aqueous feed.

The present invention can be carried out in an apparatus as shown in the accompanying figure. An aqueous solution of BPA and phenol for example the aqueous effluent from BPA purification process is fed via line 11 to a liquid-liquid extraction vessel 1 for extraction with toluene which is supplied to the extraction vessel 1 via line 17. The heavier aqueous phase from said extraction vessel from which BPA and phenol have been extracted is removed via line 19 for disposal or recycling. The aqueous phase may optionally be passed via line 18 to a toluene distillation vessel 4, where toluene can be recovered and recycled to said extractor. The cleaned aqueous product may then be optionally passed via line 20 through an additional purification stage 5 for example over an activated carbon adsorber or an organic resin bed which can remove additional BPA and phenol along with other contaminants. The lighter toluene phase from the extraction vessel 1 which contains the extracted BPA and phenol is passed via line 12 to a toluene distillation vessel 2 where toluene is azeotropically distilled from the BPA and phenol. Additional water, for example, from the aqueous phase from extraction vessel 1, may be added via line 21 to bring the composition in the distillation vessel 2 close to the azeotrope compostition to facilitate the complete removal of both water and toluene. A BPA and phenol solution is removed via line 13 and distilled toluene is returned via line 14 for reuse for extraction in said extraction vessel. The BPA and phenol are passed via line 13 to a phenol distillation vessel 3 and finally phenol is recovered via line 15 and BPA is recovered via line 16 for recycling or reuse.

In order that those skilled in the art may readily understand how the invention may be practiced, the following Example is given by way of illustration and not by way of limitation.

EXAMPLE

The process of the present invention may be better understood by reference to the following description of a specific embodiment as applied to the accompanying drawings. An aqueous solution of 5% BPA and 5% phenol, by weight, is fed via line 11 to a countercurrent extraction column 1 which is maintained at about 30° C. for liquid-liquid extraction using toluene. Toluene is supplied via line 17 and makeup toluene is supplied via line 18. Equal volumes of toluene and aqueous feed are used. The heavy aqueous phase from the extraction column 1 is removed via line 19 for disposal or optionally cleaned by additional processing. The lighter toluene phase from the extraction vessel 1 is passed via line 12 to a toluene distillation column 2 operating at about 112° C. and at ambient pressure. BPA and phenol are recovered as a bottom product via line 13 while toluene is passed via line 14 for recycling to the extraction column 1. The BPA and phenol are passed via line 13 to a phenol distillation column 3 operating at about 181° C. and ambient pressure. Phenol vapor is recovered via line 15 to be condensed and reused and BPA is recovered via line 16.

Other modifications and variations of the present invention are possible in light of the above teachings. It is, therefore, to be understood that changes may be made in particular embodiments described which are in the full intended scope of the invention as defined in the appended claims.

What is claimed is:

1. A continuous process for extracting and recovering BPA and phenol from an aqueous effluent stream which after treatment can be disposed of in an environmentally safe manner which initially consists essentially of an aqueous solution or suspension having up to 10% by weight of BPA and up to 5% by weight of phenol which is generated during the manufacture of BPA as a result of the washing of BPA adduct having at least 1 mole of phenol per mole of BPA, which comprises, (1) countercurrently extracting the aqueous effluent stream in an extraction vessel with toluene,
   (2) removing the resulting heavier aqueous phase from the bottom of the extraction vessel, while directing the upper toluene phase to a toluene distillation column, (3) distilling the toluene phase to produce a phenol and BPA bottoms product, while recycling the distilled toluene to the extraction vessel of (1), (4) directing the BPA and phenol bottoms product to a phenol distillation column, (5) recovering phenol as a condensed vapor and BPA as a bottoms product, (6) directing the aqueous phase of (2) to a distillation column to effect the separation and recovery of trace amounts of toluene from the aqueous phase and (7) passing the resulting aqueous phase from (6) through an activated carbon adsorber or an organic resin prior to disposal.

2. The process of claim 1 wherein the extraction vessel is operated at between about 20° C. and about 80° C.

3. The process of claim 1 wherein the extraction vessel is operated at temperatures between 25° C. and 35° C.

4. The process of claim 1 wherein the extraction vessel is operated at about 30° C.

5. The process of claim 1 wherein BPA and phenol are separated from the toluene stream containing PBA and phenol in a distillation vessel which is operated at about 112° C. and about 1 atmosphere pressure.

6. The process of claim 1 wherein the BPA is separated from the phenol in a distillation vessel which is operated at about 180° C. and at about 1 atmosphere pressure.

* * * * *